United States Patent [19]

Bonnefous et al.

[11] Patent Number: 5,109,856
[45] Date of Patent: May 5, 1992

[54] DEVICE FOR MEASURING THE SPEED OF MOVING ORGANS AND BLOOD FLOWS BY ULTRASONIC ECHOGRAPHY

[75] Inventors: Odile Bonnefous, Nogent sur Marne; Frédéric Mangotte, Creteil, both of France

[73] Assignee: U.S. Philips Corporation, New York, N.Y.

[21] Appl. No.: 653,821

[22] Filed: Feb. 11, 1991

[30] Foreign Application Priority Data

Feb. 9, 1990 [FR] France .................. 90 01530

[51] Int. Cl.$^5$ .............................................. A61B 8/00
[52] U.S. Cl. .......................... 128/660.01; 128/661.07; 73/861.25
[58] Field of Search ......... 128/660.01, 661.07–661.10; 73/861.25

[56] References Cited

U.S. PATENT DOCUMENTS

| | | | |
|---|---|---|---|
| 4,569,356 | 2/1986 | Kyozuka | 128/661.07 X |
| 4,744,367 | 5/1988 | Kodama et al. | 128/661.09 |
| 4,803,990 | 2/1989 | Bonnefous et al. | 128/661.08 |
| 4,809,249 | 2/1989 | Barnes | 128/661.08 X |
| 4,883,060 | 11/1989 | Pesque et al. | 128/660.01 |

OTHER PUBLICATIONS

P. Atkinson & J. P. Woodcock, "Doppler Ultrasound and Its Use in Clinical Measurement", Academic Press, 1982, pp. 125-128.

Primary Examiner—Francis Jaworski
Attorney, Agent, or Firm—William Squire

[57] ABSTRACT

A first channel processes a received echo signal and comprises a first intercorrelation circuit for two successive echographic signals $S_n(t)$ and $S_{n+1}(t)$. A second, parallel channel comprises two symmetrical parallel bandpass filters responsive to the echographic signals for generating from each received signal two signals at a frequency $f_1 < f_o$ and $f_2 > f_o$, respectively, and supplying $s_{n1}(t)$ and $s_{n2}(t)$. A multiplier forms $sS_{n1}(t) \times s_{n2}(t)$. A symmetrical low-pass filter selects the components $s_n(t)$ having the frequency $f_2 - f_1$ of the multiplier product. A second intercorrelation circuit provides a correlation signal from the selected signal $s_n(t)$ and $s_{n+1}(t)$. A multiplexing/interpolation circuit supplies the value of the speed by searching for the maximum of the first correlation function in the vicinity of the maximum of the second correlation function.

10 Claims, 2 Drawing Sheets

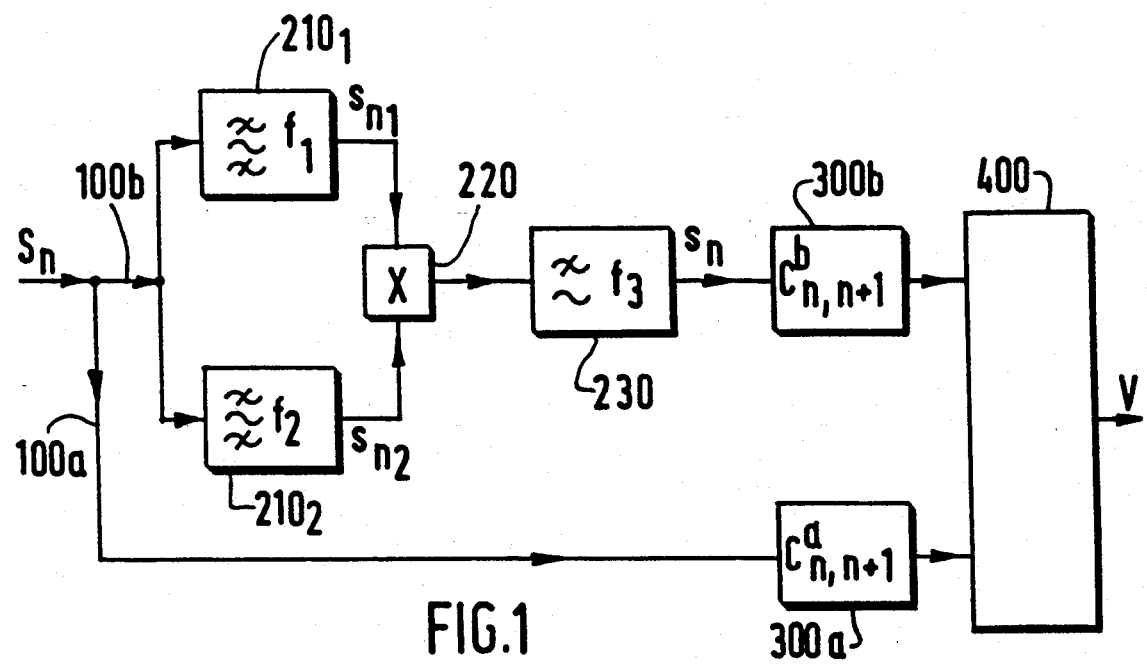
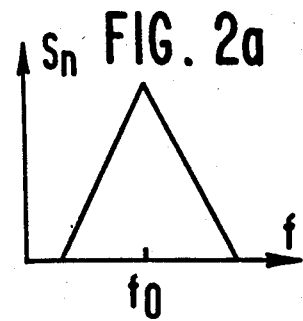
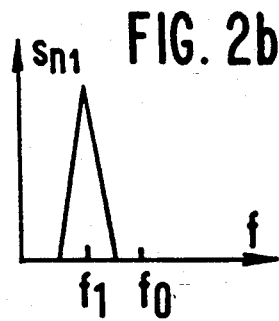
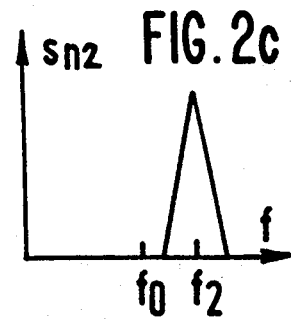
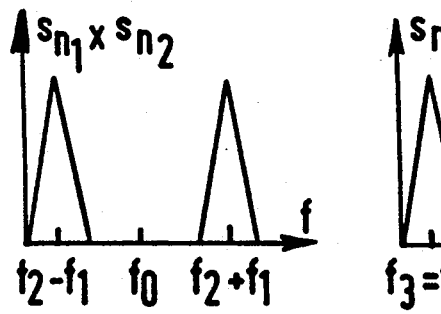
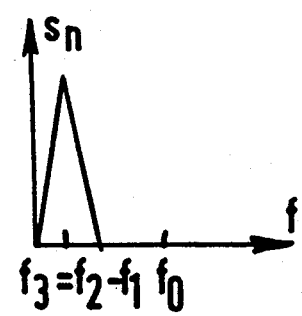

DEVICE FOR MEASURING THE SPEED OF MOVING ORGANS AND BLOOD FLOWS BY ULTRASONIC ECHOGRAPHY

FIELD OF THE INVENTION

The invention relates to a device for measuring the speed of moving organs and blood flows by ultrasonic echography, using an acoustic wave having the frequency $f_0$, which device comprises a first processing channel for the echographic signal received, which channel comprises a first intercorrelation circuit which supplies $2I+1$ sampled values of the correlation function of two successive echographic signals $S_n(t)$ and $S_{n+1}(t)$.

The invention can be used particularly attractively for the echographic scanning of moving organs, such as the walls of the heart, and blood flows in the vessels.

Of interest is commonly owned copending U.S. Ser. No. 619,276 entitled "Device for Measurement and Display of Physiological Parameters of a Blood Flow by Ultrasonic Echography" filed Nov. 28, 1990 in the name of Bonnefous.

BACKGROUND OF THE INVENTION

The general technical problem to be solved by any device for measuring of the speed of moving organs and blood flows is to obtain an exact as possible estimate of the axial speed of the movement being studied in order to form, using imaging devices, exact images of the organs and the blood flows studied by ultrasonic echographic scanning.

Various solutions to this problem have already been proposed. For example, European Patent Application No. 0 225 667 which corresponds to U.S. Pat. No. 4,885,990 describes such a device the measuring the speed of moving organs and blood flows which are backscattered by a moving target are inked by the following equation when the transmission is recurrent with a recurrent period T:

$$S_{n+1}(t) = S_n(t-\tau). \quad (1)$$

This means that the signal $n+1$ is the replica of the preceding signal n, except for a time shift $\tau$. The latter represents the additional time necessary for the ultrasonic wave to follow the path between the transducer, the target and the transducer from one activation to the next. In other words:

$$\tau = 2VT/C$$

where V is the speed of the target and C is the speed of sound. It appears that measurement of $\tau$ enables measurement of the speed V.

The intercorrelation function between $S_n(t)$ and $S_{n+1}(t)$ defined by:

$$C_{n,n+1}(to,u) = \int_{to}^{to+W} S_{n+1}(t+u) S_n(t) dt$$

verifies that:

$$C_{n,n+1}(to,u) = C_{nn}(to, u-\tau)$$

The time $to$ is linked to the scanning depth z as $to = 2z/C$, and W is the integration window.

The function $C_{nn}(to, u)$ is an autocorrelation function and is, therefore, maximum for $u=o$. Thus, the time shift $\tau$ and hence the speed V can be measured by searching the parameter u for which the function $C_{n,n+1}(to, u)$ is maximum. Therefore, the intercorrelation function is sampled with a sampling step $\Delta t$, between $u_{min} = -I\Delta t$ and $u_{max} = I\Delta t$ in steps of 1 so as to obtain $2I+1$ correlation function values. The maximum value of these $2I+1$ values, corresponding to $u=uo$, enables measurement of $\tau$ by utilizing the equality $\tau = uo$.

In order to eliminate errors inherent of the sampling during the determination of the maximum of the correlation function, use can be made of a multiplexing/interpolation circuit which supplies a more exact estimate of the speed and the corresponding peak value on the basis of correlation function values. French Patent Application No. 2 590 790 which also corresponds to U.S. Pat. No. 4,803,990 describes an example of this type of echographic signal processing where the correlation between signals is a so-called "1-bit" correlation in a sense that the signals $S_{n+1}$ and $S_n$ previously used are reduced to the sign of the ultrasonic signal. It is known that in that case the correlation function peak is shaped as an isosceles triangle. Knowledge of this shape enables complete reconstruction of the correlation peak, starting from the highest point and its two neighbors, and using linear interpolation, and hence exact determination of the position of uo.

This known method for the measurement of speeds, based on the analysis of the time shift, has substantial advantages over other methods which are based, for example on the frequency or phase shift. It notably enables the use of wideband transmission signals offering a suitable axial resolution of the measurement.

However, the method described above does not enable measurement of speeds higher than a speed limit $V_{lim}$ which is given by:

$$V_{lim} = \frac{C}{4} \cdot \frac{1}{f_0 T}$$

where C represents the propagation speed of the ultrasonic wave. This phenomenon, also known as "aliasing", is linked to the indetermination induced by the periodicity of the echographic signal. A detailed description thereof is given in "Doppler Ultrasound and Its Use in Clinical Measurement", P. Atkinson and J. P. Woodcock, Academic Press, 1982.

For example, for a recurrent period T of 100 µs a central acoustic frequency $f_n$ of 5 MHz, and a propagation speed C of 1500 m/s, a limit speed $V_{lim}$ of 75 cm/s is obtained, whereas, for example, given blood flows can reach speeds which are substantially higher.

In order to increase the measuring limit speed, it could be contemplated to reduce the frequency $f_0$, but that would lead to a reduction of the precision of measurement and the resolution. Likewise, an increase of the recurrent frequency would have the undesirable effect of a decreased scanning depth.

SUMMARY OF THE INVENTION

Thus, the technical problem to be solved by the present invention is to provide a device for measuring the speed of moving organs and blood flows of the kind set forth which enables an increase of the measuring limit C speed $V_{lim}$ without reducing the frequency $f_0$ and without increasing the recurrent frequency $1/T$.

The solution to the described technical problem in accordance with the invention includes a device which comprises a second channel for the processing of the echographic signal received, comprising:

- two symmetrical bandpass filters which act on the signal $S_n(t)$, are connected in parallel, and supply signals $s_{n1}(t)$ and $s_{n2}(t)$ which are centered around a frequency $f_1$, being at the most equal to $f_0$, and around a frequency $f_2$, being at least equal to $f_0$, respectively, the difference $f_2-f_1$ being smaller than $f_0$,
- a multiplier which forms the product of the signals $s_{n1}(t)$ and $s_{n2}(t)$,
- a symmetrical bandpass filter which selects the component $s_n(t)$ having the frequency $f_2-f_1$ of the product $$s_{n1}(t) \times s_{n2}(t),$$

a second intercorrelation circuit which supplies $2I+1$ sampled values of the correlation function of two successive signals $s_n(t)$ and $s_{n+1}(t)$, referred to as the second correlation function,
and in that a multiplexing/interpolation circuit supplies an estimate of the speed by searching the maximum of the first correlation function around the sample offering the highest value of the second correlation function.

Thus, the device in accordance with the invention utilizes not only a signal $S_n(t)$ of high frequency ($f_0$) as in the known device, but also a second signal $S_n(t)$ of low frequency ($f_2-f_1$) which also satisfies the relation (1) and which can thus be treated as the signal $S_n(t)$.

Because the filters used for forming the low-frequency signal are symmetrical and do not introduce delays or phases in the frequency domain, and because the calculation of the correlations takes place in the same circumstances for both signals, the two correlation functions (the first and the second function) coincide exactly, the maximum of one function corresponding to the maximum of the other function. The two correlation functions differ in that the first function, linked to the signal $S_n(t)$, has a higher frequency and presents more pronounced peaks than the second function, resulting in a higher measuring precision, while the second correlation function, being linked to the signal $S_n(t)$, has a frequency which is much lower and presents substantially only one maximum in the measuring range considered. Using the second correlation function, this enables complete elimination of the indetermination due to the "aliasing" effect in the measurement of the speed on the basis of the first correlation function.

In conclusion it can be observed that the device in accordance with the invention combines the advantages of a high measuring speed, determined by the high-frequency signal, and a higher speed limit which is enabled by the low-frequency signal and whose value is given by:

$$V_{lim} = \frac{C}{4} \frac{1}{(f_2-f_1)T}$$

It is also to be noted that, apart from of the "aliasing" phenomenon, the device in accordance with the invention also enables elimination of other ambiguities which are linked to the sampling during the determination of the correlation peak. It may actually occur that the highest point of the correlation function sampled does not relate to the correlation peak searched. This situation may occur when complex flows are measured which comprise considerable speed gradients which tend to lower the correlation peak. This error becomes apparent as abrupt discontinuities in the reconstruction of the speed profile as a function of the scanning depth.

IN THE DRAWING

The invention will be described in detail hereinafter, by way of example, with reference to the accompanying drawings.

FIG. 1 shows the diagram of a device for measuring the speed in accordance with the invention.

FIG. 2 diagrammatically shows the spectra of the signals involved in the operation of the device shown in FIG. 1.

FIG. 3 shows examples of correlation functions obtained by means of the device shown in FIG. 1 and also shows their use for the desired measurement of the speed.

DESCRIPTION OF THE PREFERRED EMBODIMENT

Figures 3A, 3B, 3C:
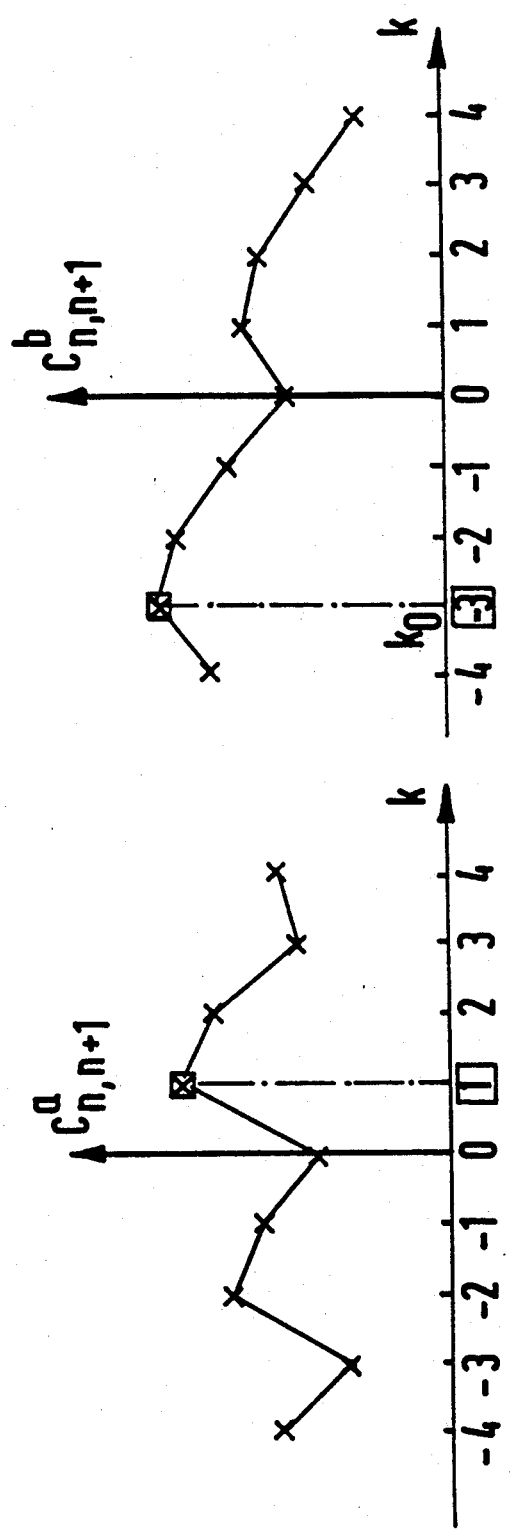

FIG. 1 diagrammatically shows a device for measuring the speed of moving organs and blood flows. This device forms part of an ultrasonic echographic scanning apparatus which also comprises (not shown in FIG. 1), at least one ultrasonic transducer which supplies an acoustic wave which is centered around a frequency $f_0$ of, for example 5 MHz, a stage for the periodic transmission by the transducer of a pulse signal having a given recurrent frequency $F=1/T$ of, for example 10 kHz, and a stage for receiving echographic signals returned to the transducer and for processing the signals received. The aforementioned European Patent Application No. 0 225 667 contains a detailed description of these various stages. The receiving and processing stage comprises a fixed-echo elimination device enabling an echographic signal $S_n(t)$ having the frequency $f_0$ to be obtained wherefrom disturbing echoes originating from reflections from the fixed walls of organs or vessels have been removed. The frequency spectrum of the signal $s_n(t)$ is diagrammatically shown in FIG. 2a. As appears from FIG. 1, the signal $S_n(t)$ is applied, via a first processing channel 100a, to a first intercorrelation circuit 300a which comprises, in a conventional manner, a delay line having a recurrent period $T$ which enables simultaneous reception of two consecutive signals $S_n(t)$ and $S_{n+1}(t)$. Subsequently, $2I+1$ delay lines shift one of the two signals with respect to the other signal by an amount $u_k=k\Delta t$, where $k$ is an integer number taking the values $-I, -I+1, \ldots, -1, 0, 1, \ldots, I-1, I$, and $\Delta t$ is the sampling step, for example 50 ns. Finally, $2I+1$ correlators supply $2I+1$ sample values of the first correlation function, so:

$$C^a_{n,n+1}(t_0, u_k) k \in [-I, I]$$

An example of such a correlation function is given in the FIGS. 3a and 3c, where I equals 4.

The device shown in FIG. 1 also comprises a second channel 100b for the processing of the echographic signal received, comprising:

- two symmetrical bandpass filters $210_1$, $210_2$ which act on the signal $S_n(t)$, are connected in parallel, and supply signals $s_{n1}(t)$ and $s_{n2}(t)$, respectively, which are centered around a frequency $f_1$ which at the most equals $f_0$, for example 4 MHz, and a frequency $f_2$ which is at least equal to $f_0$, for example 6 MHz, respectively, the difference $f_2-f=2$ MHz being smaller than $f_0=5$ MHz. It is to be noted that the frequencies $f_1$ and $f_2$ must be situated, as indicated in the FIGS. 2b and 2c, in the ultrasonic frequency band centered around $f_0$.

Symmetrical filters are to be understood to mean filters whose time response $h(t)$ satisfies $h(-t)=h(t)$. On the other hand, the signals $s_{n1}(t)$ and $s_{n2}(t)$ satisfy the above general relation (1).

a multiplier 220 which forms the product of the signals $s_{n1}(t)$ and $s_{n2}(t)$, thus producing two signals in the frequency spectrum (FIG. 2d), one signal having a low frequency which is centered around $f_2-f_1$, the other signal having a high frequency which is centered around $f_2+f_1$.

a low-pass filter (230) which is also symmetrical and which selects the component $s_n(t)$ having the frequency $f_3=f_2-f_1$ of the product $s_{n1}(t)\times s_2(t)$ as can be seen in FIG. 2e.

a second intercorrelation circuit 300b which is analogous to the circuit 300a of the first processing channel 100a and which supplies 2I+1 sampled values, which the sampling step $\Delta t$, of the correlation function $C_n^b{}_{,n+1}(t_0, u_k)$ of two successive signals $s_n(t)$ and $s_{n+1}(t)$. FIG. 3b shows an example of the second correlation function $C_n^b{}_{,n+1}(t_0, u_k)$ which, as can be seen, has a frequency which is lower than the first correlation function $C_n^a{}_{,n+1}$.

The correlators used in the intercorrelation circuits 300a and 300b may be so-called 1-bit correlators, as mentioned above, which impart a triangular shape to the correlation functions of FIG. 3.

At the output of the intercorrelation circuits a multiplexing/interpolation circuit 400 supplies an estimate of the speed V by searching the maximum of the first correlation function $C_n^a{}_{,n+1}$ around the sample ko producing the highest value of the second correlation function $C_n^b{}_{,n+1,n+1}$. FIG. 3 illustrates this procedure for a concrete example. The first correlation function $C_n^a{}_{,n+1}$ has two relative maximum values for the samples $k=-2$ and $k=1$ and, the maximum value at $k=1$ being the highest value, it could be thought that the speed V is near $kC\Delta t/2T$, so $C\Delta t/2T$. Actually, the second correlation curve $C_n^b{}_{,n+1}$ removes this indetermination, because it clearly indicates that the calculation of the speed should take place around the sample $k_0=-3$, imposing the sample $k=-2$, second maximum value of $C_n^a{}_{,n+1}$. The linear interpolation for determining the position of the maximum of $C_{na,n+1}$ more exactly around $k=-2$ is performed utilizing 5 samples enclosing $k=-2$, so $-4, -3, -2, -1, 0$. This number of 5 points is chosen because of the fact that in the present example the sampling frequency $1/\Delta t$ amounts to 4 times the frequency $f_0$; thus, 5 samples can be taken in one period of the ultrasonic signal. This linear interpolation, being linked to the 1-bit correlation, reconstructs the isosceles triangle on the basis of the maximum point and its two neighboring points. Using the aforementioned values for $f_0$, $f_1$ and $f_2$, it appears that the limit value $V_{lim}$ of the speed is multiplied by $f_0/(f_2-f_1)$, so 2.5. Speeds in the vicinity of 200 cm/s, meaning any speed of movement or flow occurring in the human body, can thus be obtained.

What is claimed is:

1. A device for measuring the speed of moving organs and blood flows by ultrasonic echography, using an acoustic wave having a central frequency $f_o$, said device comprising a first processing channel means for the echographic signal received, which channel means comprises first intercorrelation means which supplies 2I+1 samples values of the correlation function of two received successive echographic signals $S_n(t)$ and $S_{n+1}(t)$, referred to as the first correlation function of different values, the maximum value of which is at a set of coordinates, second processing channel means for the echographic signal received, comprising:

two parallel symmetrical bandpass filter means which act on the signal $S_n(T)$ applied thereto to supply signals $S_{n1}(t)$ and $S_{n2}(t)$, respectively, which are centered around a frequency $f_1$, being at the most equal to $f_o$, and around a frequency $f_2$, being at least equal to $f_o$, respectively, the difference $f_2-f_1$ being smaller than $f_o$, multiplier means which form the product of the signals $S_{n1}(t)$ and $S_{n2}(t)$, symmetrical bandpass filter means which selects the component $S_n(t)$ having the frequency $f_2-f_1$ of the product $S_{n1}(t)\times S_{n2}(t)$, second intercorrelation means for supplying 2I+1 sampled values of the correlation function of two successive signals $S_n(t)$ and $S_{n+1}(t)$, referred to as the second correlation function, and multiplexing-/interpolation means for supplying an estimate of the speed by searching the coordinates of the maximum value of the correlation function around the sample offering the highest value of the second correlation function.

2. A device as claimed in claim 1 wherein said intercorrelation means comprise 1-bit correlators, and in that said multiplexing/interpolation means includes means for performing an interpolation reconstruction of an isosceles triangle.

3. A device for measuring the speed of moving organs and blood flow by ultrasonic echography using an acoustic wave having a central frequency $f_o$ comprising:

a first signal processing channel for processing a received echographic signal, said first channel comprising first intercorrelation means for supplying sampled values of the correlation function of two successive received echographic signals forming a first correlation function signal of differing values having a maximum value at a set of coordinates;

a second signal processing channel for processing said received echographic signal, said second processing channel comprising:

means for forming a received echographic signal into two signals each centered about a corresponding respective first and second frequency $f_1$ and $f_2$, the first frequency being at most $f_o$ and the second frequency being at least equal to $f_o$, the difference between $f_1$ and $f_2$ being smaller than $f_o$, the means for forming including means for forming the product of said two signals into first and second components and for selecting one of said components;

second intercorrelation means for supplying a plurality of sampled values of the correlation function of said selected one component of said received two successive signals forming a second correlation function signal of differing values; and means responsive to said first and second correlation function signals applied thereto for supplying an estimate of the speed corresponding to the coordinates of the maximum value of the first correlation function signal around the sample having the highest value of the second correlation function signal.

4. The device of claim 3 wherein said means for forming said received signal into two signals includes two symmetrical bandpass filters connected in parallel, each filter forming a different one of said two signals.

5. The device of claim 3 wherein said means for forming said product includes multiplier means for multiplying said two signals.

6. The device of claim 5 wherein said means for selecting said one component includes symmetrical bandpass filter means responsive to said components applied as an input thereto for selecting the signal of lower frequency.

7. The device of claim 3 wherein said first and second intercorrelation means each includes 1-bit correlating means which form said correlation functions into triangular functions.

8. A device for measuring the speed of moving organs and blood flow by ultrasonic echography using an acoustic wave having a central frequency $f_o$ comprising:
a first signal processing channel for processing a received echographic signal, said first channel comprising first intercorrelation means for supplying sampled values of the correlation function of two successive related echographic signals forming a first correlation function signal of differing values having a maximum value at a set of coordinates;
a second signal processing channel for processing said received echographic signal, said second processing channel comprising:
means for forming said received echographic signal into two signal components, each centered about corresponding respective first and second spaced frequencies $f_1$ and $f_2$ and for selecting one of said components;
second intercorrelation means for supplying a plurality of sampled values of the correlation function of said selected one component forming a second correlation function signal of differing values; and
means responsive to said first and second correlation function signals applied thereto for supplying an estimate of the speed corresponding to the coordinates of the maximum value of the first correlation function signal around the sample having the highest value of the second correlation function signal.

9. The device of claim 8 wherein said means for forming said components includes two symmetrical bandpass filters responsive to the received echographic signal connected in parallel and which supply corresponding two signals centered respectively about a frequency $f_1$ and $f_2$, said means for selecting including multiplier means for forming the product of said latter two signals into said two signal components and symmetrical bandpass filter means for selecting one of said two signal components.

10. The device of claim 9 wherein said frequency $f_1$ is at most equal to $f_o$ and said frequency $f_2$ is at least equal to $f_o$, the difference between $f_1$ and $f_2$ being smaller than $f_o$.

* * * * *